US006855734B2

(12) United States Patent
Messadek

(10) Patent No.: US 6,855,734 B2
(45) Date of Patent: Feb. 15, 2005

(54) GLYCINE BETAINE AND ITS USE

(76) Inventor: Jallal Messadek, Place des Bequinages 2, B-4000 Liege (BE)

( * ) Notice: Subject to any disclaimer, the term of this patent is extended or adjusted under 35 U.S.C. 154(b) by 101 days.

(21) Appl. No.: 09/945,391

(22) Filed: Aug. 31, 2001

(65) Prior Publication Data

US 2002/0065320 A1 May 30, 2002

Related U.S. Application Data

(63) Continuation-in-part of application No. PCT/BE00/00021, filed on Mar. 1, 2000.

(51) Int. Cl.$^7$ ...................... A61K 31/205; A61K 38/48; A61K 31/198; C07K 14/745; C07K 38/36

(52) U.S. Cl. .......................... 514/561; 514/23; 514/77; 514/556; 514/578; 514/824; 514/834; 514/457; 514/571; 514/161; 514/165; 514/554; 514/423; 514/460; 424/400; 424/443; 424/422; 424/464; 424/94.64

(58) Field of Search .................................. 514/561, 554, 514/23, 165, 77, 161, 556, 571, 578, 457, 824, 834, 423, 460; 424/400, 443, 422, 464, 94.64

(56) References Cited

U.S. PATENT DOCUMENTS 5,880,098 A * 3/1999 Haussinger ................... 514/23

FOREIGN PATENT DOCUMENTS

| EP | 0347864 | 6/1989 |
|---|---|---|
| EP | 0781554 | 7/1996 |
| HU | 210122 B | 9/1992 |
| WO | 9515750 | 12/1993 |
| WO | 9738685 | 4/1996 |
| WO | 9706795 | 8/1996 |
| WO | 9819690 | 11/1996 |
| WO | WO 97/06795 | * 2/1997 |
| WO | 0025764 | 10/1998 |

OTHER PUBLICATIONS

Mar et al., Betaine in wine: answer to the French paradox., Med Hypothesis, Nov. 1999.; 53(5):383–5, see abstract.*
Changes in blood coagulation in experimental subacute poisoning with p–chlorobenzene. The influence of some lipotropic factors, Folia Medica (Naples), 1960, 43, 259–66, see: abstract.*
Article from Entrez–PubMed web page entitled: SR 121787, a new orally active fibrinogen receptor antagonist.
Article from Entrez–PubMed web page entitled: Antiaggregatory, antithrombotic effects of MS–180, a novel platelet glycoprotein llb/llla receptor antagonist.
Article from Entrez–PubMed web page entitled: Antithrombotic effects of MK–0852, a platelet fibrinogent receptor antagonist, in canine models of thrombosis.

Article from Entrez–PubMed web page entitled: SR 121787, Prevention of thrombosis and enhancement of thrombolysis in rabbits by SR 121787, a glycoprotein ll/lll antagnoist.
Article from Entrez–PubMed web page entitled: Role of platelets in thrombosis and hemostasis.
Article from Entrez–PubMed web page entitled: Nonpeptide glyocprotein llb/llla inhibitors. 5. Antithrombotic effects of MK–0383.
Article from Entrez–PubMed web page entitled: The in vitro and in vivo pharmacological profiles of a platelet glycoprotein llb/llla antagonist, NSL–9403.
Article from Entrez–PubMed web page entitled: antiplatelet and antithrombotic effects of orbofiban, a new orally active GPllb/llla antagonist, in guinea pigs.
XP–002123170 Database Chemabs 'Online!; Chemical Abstracts Service, Columbus, OH Zapadnyuk, B.I. et al.: "Bile–secretory effect of trimethylglycine in normal and atherosclerotic animals of different ages" retrieved from STN Database accession No. 107:190742 HCA abstract & Byull. Eksp. Biol. Med. (1987), 104(7), 30–2.
XP002123171 Database Chembas 'Online!; Chemical ABstracts Service, Columbus, OH Panteleimonova, T.N. et al.: "Effect of trimethylglycine on lipid metabolism in rabbits with experimental atheroscrlerosis" retrieved from STN Database accession No. 99:99080 HCA abstract & Farmakol. Toksikol. (Moscow) (1983), 46(4), 83–5.
XP–000853747 Fazio B et al: "Treatment of human atherosclerosis with betaine." Minerva Med, (Apr. 25, 1961) 52 1511–6., the whole document.
XP–002123167 P.H. List et al.: "Hagers Handbuch Der Pharmazeutischen Praxis" 1972, Springer–Verlag, Berlin Heidelberg, New York, p. 431.
XP00085853 "Betaine for homoceystinuria." Medical Letter on Drugs and Therapeutics, (1997) 39/993 (12)., the whole document.
Xp000853897 Wilcken D E et al: "The natural history of vascular disease in homocystinuria and the effects of treatment." Journal Of Inherited Metabolic Disease, (Jun. 1997)20 (2) 295–300., the whole document.
XP–002123168 J.E.F. Reynolds: "Martindale, The Extra Pharmacopoeia" 1996, Royal Pharmaceutical Society, London "Betaine hydrochloride" p. 1679.
XP002123169 "the merck index" 1996, Merck & Co, Whithouse Stations, NJ "Betain" p. 198.

(List continued on next page.)

Primary Examiner—Frederick Krass
Assistant Examiner—Clinton Ostrup
(74) Attorney, Agent, or Firm—Hovey Williams LLP

(57) ABSTRACT

Pharmaceutical uses of glycine betaine, such as for the treatment of thromboses not induced by hyperhomocystenemia or homocystinuria, of blood disorders, such as blood coagulation, thrombi formation.

48 Claims, No Drawings

OTHER PUBLICATIONS

Matthews, et al.; An indirect response model of homocysteine suppression by betain: optimising the dosage regimen of betaine in homocystinuria: 2002 Blackwell Science Ltd Br; J Clin Pharmacol, 54, 140–146.

Schwahn et al.; Pharmacokinetics of oral betaine in healthy subjects and patients with homocystinuria; 2003 Blackwell Science Ltd Br; J Clin Pharmacol, 55, 6–13.

Da Silva; Anticoagulants: to bleed or not to bleed, that is the question.; SUNY Upstate Medical University Syracuse, NY, USA; Semin Vasc Surg. Dec. 2002; 15(4): 256–67; PMID: 12478500 (PubMed– indexed for MEDLINE).

Silver; The caput medusae of hypercoagulability.; Department of Surgery, University of Missouri–Columbia, USA; Vasc Surg. Feb. 2000; 31 (2): 396–405; PMID: 10664508 (PubMed—indexed for MEDLINE).

Rogers; Hypercoagulable states.; Section of Endocrinology and Metabolism, West Virginia University Health Sciences Center.; W V Med J. Feb. 1993; 89(2): 61–3; PMID: 8442350 (PubMed—indexed for MEDLINE).

Marcel et al.; From Virchow to red cells (the unended quest).; Ric Clin Lab. 1983; 13 Suppl 3:71–81.; PMID: 6324327 (PubMed—indexed for MEDLINE).

Lasch; (Principles of drug prevention of thrombosis); (Article in German); Langenbecks Arch Chir. 1986, 369: 451–7; PMID: 3807563 (PubMed–indexed for MEDLINE).

Copy of a Chinese document (Homocysteine and Vascular Diseases) Subdivision of Foreign Medical Surgery, 1996. 23, 2 pages 91–93, as well as an English translation thereof. An English translation of BE 09900141 (sent via facsimile).

* cited by examiner

GLYCINE BETAINE AND ITS USE

This is a continuation-in-part of International Application PCT/BE00/00021 filed Mar. 1, 2000, and published in French (and not in English) under PCT Article 21(2) as International Publication No. WO 00/51596 on Sep. 8, 2000, Which Claims Priority under Pct Rule 4.10 from Belgian Application Serial No. 9900144 filed Mar. 2, 1999.

FIELD OF THE INVENTION

This invention relates to the use of glycine betaine to eliminate physiopathological vascular attacks. The invention relates to the curative and preventive activity of glycine betaine in the pathogenesis of thrombo-embolic and haemostatic diseases of arterial or venous origin.

Glycine betaine exhibits preventive activity while preventing the formation of thrombi and exhibits a curative activity which prevents the proliferation of thrombi while destroying them. The significance of the present invention is based on the fact that the use of glycine betaine does not result in any risk of haemorrhage or allergy in opposition to the molecules and treatments currently used.

PRIOR ART

Vascular thromboses are a response of the organism which is facing attack on a vessel wall and on the content of cells and plasma thereof. Thrombosis is a localised activation of coagulation with the formation of a thrombus.

The interest to which this pathology has been subjected in recent years has enabled several causative factors to be identified:

the vessel, the vascular wall and the endothelial cells, the role of elements which occur in blood the coagulation of fibrinolysis systems, and inhibitors thereof.

Several types of thromboses exist which can occur in arteries, in veins, in the microcirculation of the organs, in the cavities of the heart and at artificial surfaces in contact with blood. Vascular thromboses are a response to the attack on the vessel wall and on its content of cells and plasma. A thrombosis is an organized mass of blood elements (platelets, red corpuscles and white corpuscles), of fibrin and of other plasma proteins, which are deposited at the surface or which obstruct the free passage of the vascular system.

The mechanisms of thrombosis resemble those of haemostatis, but are pathological due to their abnormal intravascular location.

Thromboses and embolisms are the main reasons for clinical complications associated with cardiovascular diseases and atherosclerosis.

According to Virchow, at least three types of thrombogenetic factors determine the location, the extent and the regression of a thrombosis:

haemodynamic and rheological factors;

endothelial lesion;

activation of the constituents of blood, particularly of platelets, and of coagulation which results in the formation of thrombin.

Thrombo-embolic disease of arterial or venous origin remains one of the main reasons of death in developed countries.

Arterial thrombosis is often due to a rupture of the atherosclerotic plaque, whereas venous thrombosis results from a deficit of a coagulation inhibitor (AT III) or from a deficit of a fibrinolysis activator (S protein and/or C protein) or more frequently from stasis. In fact, both of these result from an interaction between blood and the vascular wall, from the formation of a venous thrombosis and/or from a haemostatic anomaly. Arterial thrombosis is more often secondary to a parietal anomaly and mainly involves blood platelets. It contributes to a wide variety of clinical pictures depending on the arterial layers involved in the interruption of vascularisation. Thrombosis is mainly capable of affecting the cardiac arteries (coronary), and the arteries of the lower, cerebral or digestive organs. Thus arterial disease favours the formation of the thrombus itself which is responsible for the majority of terminal vascular occlusions. Moreover, participation of haemostatic disorders and of the thrombus formed at other vascular lesions is evident: aggravation of the lesions of the vascular wall, ischemia and problems in the microcirculation.

Three therapeutic strategies can be distinguished for the prevention of accidents associated with thromboses:

Anticoagulants. These constitute the major element in the treatment of a patient exhibiting a thrombo-embolic disorder. Heparin and derivatives thereof are currently used. However, the use of heparins can give rise to two major complications, namely haemorrhage or thrombopenia.

K antivitamins (KAV). Prescribed for long-term treatment, these cannot be used in an emergency and cannot be prescribed simultaneously with other anti-aggregants, since they potentiate the haemorrhagic effect thereof.

Platelet antiaggregants. Prescribed to prevent arterial thrombosis associated with atherosclerosis. The main inhibitors of platelet functioning which are currently prescribed are: aspirin, ticlopidine, dipyridamole, and certain non-steroid anti-inflammatory agents such as flurbiprofen and prostacyclin. These treatments are really effective, but have undesirable effects on patients subject to allergies or haemorrhage.

Despite their efficacy, all these treatments necessitate special precautions in use, such as the administration of antidotes, overdose problems and unwanted side effects. These treatments make it necessary to monitor patients, due in particular to haemorrhage-related problems which can arise during or after medication, as well as possible incompatibility with other drugs. It was therefore of interest to identify a molecule having a high antithrombotic potential without undesirable effects. Most surprisingly, glycine betaine has been identified as possessing a high therapeutic potential for in the treatment of thromboses.

Glycine betaine, or betaine of formula $(CH_3)_3N^+$—$CH_2$—$COO^-$, is a molecule known for its osmo-protective properties and for its cosmetic and pharmaceutical uses. Various pharmaceutical uses of betaine are known, particularly the use of betaine for the treatment of homocistinuria, which causes cardiovascular problems (L. & B. Wilken, J. Inher. Metab. Dis. 1997). Thus patients suffering from homocistinuria, which is a genetic anomaly, exhibit premature atherosclerotic and thrombo-embolic disorders (S. H. Mudd et al., The metabolism and molecular bases of inherited disease, 1995), and of cardiovascular diseases (McCully, Atherosclerosis Rev. 11, 1983). Homocistinuria is a hereditary deficiency, the homozygotic form of which is rare. It is estimated that the prevalence of this homozygotic form corresponds to 1 in 200 in the general population.

Homocistinuria is due to elevated levels of homocysteine in the plasma of the affected patient. The administration of betaine enables the concentration of homocysteine in the blood to be reduced.

Publication WO 951 157 50 proposes the use of ingredients comprising betaine in order to prevent vascular disorders in homocistinuric patients.

Publication WO 98/19690 also relates to patients suffering from an elevated homocysteine level in their blood. The use of betaine amongst other ingredients is intended to reduce the level of homocysteine in the blood, it having been established that homocysteine is a positive factor of risk in the occurrence of cardiovascular diseases, as well as in Alzheimer's disease.

Publication EP 0 347 864 describes the use of betaine together with other ingredients in order to combat the increase in sulfhydryl groups, which are due to cysteine and to homocysteine, in human plasma, and thus to inhibit the formation of atherosclerotic plaques.

This anti-atherosclerotic effect is known and is extensively documented. These publications relate to the effect of betaine on the metabolsim of lipids (Zapadnyuk et al. Biol. Med. 1987), and on that of cholesterol (Panteleimonova et al., Farmakol. Toksikol, Moscow 1983).

Publication WO 97 38685 describes the use of betaine and taurine for the treatment of complications resulting from ischemia in some organs. Ischemia is a localised stoppage of the bloodstream and only represents one of the pathologies due to thrombosis.

Publication EP 0 781 554 comprises examples which describe experiments on enucleated hearts, i.e. on hearts which have been extracted and isolated from the vascular system. The use of betaine for its known osmoprotective and antiradical properties enables the inventors to claims a protective action thereof on the cardiac muscle.

Other forms of betaine have been proposed (WO 97/06795), but have not hitherto equaled the potency and performance of glycine betaine.

None of these publication discloses the potency of glycine betaine with respect to venous and/or arterial thrombisis, nor its anti-aggregant and anticoagulant potency.

BRIEF DESCRIPTION OF THE INVENTION

Glycine betaine, as well as betaine compounds of the general formula $(CH_3)_3N^+-(CH_2)_n-COO^-$, with n varying from 1 to 5 (preferable equal to 1) in the context of the present invention can be used for various clinical applications, such as:

coronary thromboses and venous thromboses thromboses and re occlusion of the vascular system following a thrombolysis or an angioplasty infarct, angina pectoris, aneurysm, pulmonary embolism, phlebitis cerebral embolism post-traumatic shock, whether or not of surgical origin prevention of accidents of microcirculation in the following cases: haemophilia, chemotherapy, ageing, oral contraception using oestrogens, obesity, tobacco addiction, prosthesis, diabetes.

prevention of the risks associated with the administration of contrasting ionic and non ionic products.

The extracorporal circulation and the haemodialysis procedures. The blood in contact with artificial surfaces of patients subject to an extracorporal circulation has a risk of formation of platelet nails, of thrombi and embolism. These risks can be prevented by administering the compound(s) of the invention before and/or during and/or after these procedures.

Inflammation phenomena. When binding it with integrine of Mac-1 receptor of the leukocytes and by reducing the expression of mitogenes and pro inflammation cytokines. When acting on the Mac-1 receptor, the compounds of the invention reduce the adhesive and migration properties of the leukocytes reducing thereby the tissue aggression.

Haemostatic glues. By allowing, in function of pathologies, the gel time of the glues, while reducing secondary effects due to their uses.

Stings and bites of venomous animals. Experimental data show that the injection of compounds of the invention to rats to which a venom lethal dose is injected, delays the death thereof. The compounds of the invention are therefore suitable for entering into antidote composition for venom, possibly in combination with other antivenomous compound(s).

Prevention of blood circulation problems due to contact with artificial surfaces, such as biomaterial elements, prosthesis, etc. (cardiac valves, balloons, catheters, hip prosthesis, etc .). When coating these elements with betaine, the secondary effects are reduced.

Metastasis Prevention of cancerous cells. This anti tumoral activity is bound to the fact that cancerous cells released from tumors are transported by the micro thrombi inside the vascular system. These cancerous cells are undetectable by the immune system able to destroy them. Moreover, their incorporation in the micro thrombi facilitates their binding to the vascular system or in the organs, and creates then new cancerous colonies. As the formation of thrombi is function to the adhesion of fibrinogen to glycoprotein IIb IIIa site on the activated platelets, an antagonist of fibrinogen adhesion has an antimetastasis activity by permitting the immune system to detect the cancerous cells during their migration, and by removing the vehicle (thrombus) enabling their transport and their binding. The compounds of the invention can be administered alone or with other anticancerous compounds (simultaneous administration or not) so as to improve their efficiency and the process of angiogenesis during malignant melanomas.

Process for detecting and localizing thrombi by binding compounds of the invention to a portion detectable in vivo and/or in vitro.

Process for avoiding thromboembolitic problems correlated to air trips. In view of its very low toxicity and its blood fluidifying characteristics, the betaine can be administered in the form of sweets, confectioneries, cookies, drinks, meals, candies, etc. so as to prevent thromboembolic events for airplane/flight passengers.

Sweetener for diabetes, the betaine being or not associated with another sweetener. As Betaine is a residue of sugar production, betaine has some sweetening properties which can be used for the preparation of sweetener with anti aggregation properties. Said sweetener, while avoiding circulation problems bound to diabetes, could improve the efficiency of insulins. It has been demonstrated that the activation of vitronectin receptors facilitates the cell migration and provides the necessary signals for the regulation and proliferation of cells, and potentialises the insulin effect (Ruoslahti, Kidney Int., 1997, 51, 1413–1417)

Process for individualizing cells in culture in vitro

As anti bacterial and anti infectious

Use of a compound of the invention (compound of the general formula $(CH_3)_3N^+-(CH_2)_n-COO^-$, with n an integer from 1 to 5, preferably equal to 1, or a mixture of such compounds or one or more pharmaceutically acceptable salts, for the preparation of a pharmaceutical composition for the treatment or for the prevention of troubles bound to one or more glycoproteins, especially to the receptor of one or more glycoproteins, preferably to the receptor of glycoprotein IIb IIIa.

Use of a compound of the invention (compound of the general formula $(CH_3)_3N^+—(CH_2)_n—COO^-$, with n an integer from 1 to 5, preferably equal to 1, or a mixture of such compounds or one or more pharmaceutically acceptable salts for potentializing the therapeutical effect of a pharmaceutical active agent.

Platelet aggregation is an essential event in the formation of blood clot and thrombus. In normal conditions, following a vascular lesion, blood clots prevent blood losses by closing the opening. However, in some pathological instances, the formation of a blood clot can reduce partly or completely the blood circulation, with the consequence of a cellular necrosis.

For example, the platelet aggregation and thus the thrombosis at the level of the artherosclerosis plaques is an important factor for the genesis of conditions such as angina pectoris, myocardus infarct, vessel occlusion following a thrombolysis or an angioplasty. Patients suffering a heart attack are treated with thrombolytic agents such as plasmin activators and the streptokinases which dissolve the fibrin from the clots. A major complication of this therapy is the reocclusion of vessels due to platelet aggregation, which can lead to irreversible damages to the heart, the brain or other organs.

Thrombosis starts with the adhesion of platelets at the vascular lesion sites. The platelet adhesion is initiated by the receptor located at the surface of the platelets which bind to proteins of the extracellular cellular matrix of the exposed endothelium, such as fibrinogen, fibronectin, Von Willebrand factor, as well as other adhesive proteins such as vibronectin, collagen and laminin. Therefor, the activation of platelets is a reply to agonists such as epinephrine, ADP, collagen, the arachidonic acid or the thrombin. This activation leads to the activation of the glycoprotein Ib receptor (GP Ib) and/or of the glycoprotein IIb IIIa receptor (GP IIb IIIa) at the surface of the platelets. This receptor(s) (GP Ib and/or GP IIb IIIa) is/are then available for its/their binding to fibrinogen and the platelet aggregation. The adhesion of the receptor (GP IIb IIIa) to other adhesive proteins such as the Von Willebrand factor also leads the attachment of platelets between them and their aggregation. The adhesion of molecules such as fibrinogen or the Von Willebrand factor to the receptor (GP IIb IIIa) leading the platelet aggregation is an essential step in the formation of the thrombus. The receptor (GP IIb IIIa) is thus a privileged target for the new therapy treating thrombosis and thromboembolitic pathologies. Furthermore, the use of antagonists of the glycoprotein IIb IIIa receptor inhibits the platelet aggregation, while respecting the other hemostasis mechanisms, is highly desirable in the new therapies bound to thrombosis. Several molecules having this antagonist property are marketed with usage restrictions due to immunoreactivity problems, toxicity, allergy or hypersensibility reactions for some patients. A subject matter of the present invention is to propose a molecule, especially a well-known and used molecule of vegetal origin, having this antagonist activity for the glycoprotein IIb IIIa receptor, while not having toxic characteristics.

It is also known that the activation of the vitronectin receptor improves the cell migration and provides regulating signals of the cell proliferation and cell differentiation, and activates the effects of insulin (Ruoslahti, Kidney Int., 1997, 51, 1413–1417). The regulation of the vitronectin receptor is associated with pathological conditions, such as vascular restinosis (Clemetson and Clemetson, Cell.Mol. Life Sci., 1998, 54, 502–513), bone excess resorbtion (Rodan and Rodan, J. Endocrinol., 1997, 154 Suppl, S47–56), and the angiogenesis process during the malignant melanomas (Cheresh, Cancer Metastasis Rev., 1991, 10, 3–10).

Surprisingly, it has now been found that betaines of formula $(CH_3)_3N^+—(CH_2)_n—COO^-$, with n an integer from 1 to 5, and their pharmaceutically acceptable salts, have an antagonist activity for one or more glycoprotein(s) receptors, such as the glycoprotein Ib receptor and the glycoprotein IIb IIIa receptor, by inhibiting the platelet aggregation induced by various agonists. This antagonist activity is not restricted to the glycoprotein site IIb IIIa but to all glycoprotein sites implicated in the cell adhesion of various origins, there between.

Platelets are activated by some agonists, whereby their forms, as well as their secretions of their granules can be modified, and whereby the aggregation thereof can be induced and the formation of clots and thrombi can be produced.

Several endogenous agonists, such as ADP (adenosine-5-diphosphate), serotinine, arachidonic acid, epinephrine, adrenaline, thrombin, collagen, ristocetine are known.

Recently a mechanism of action of these agonists has been identified, namely the activation of the glycoproteic site GP IIb IIIa which causes the adhesion of the circulating fibrinogen (Thromb. Res. 1993, 72, 231–245) and therefore the consolidation of platelets groups and the formation of clot. (Drug of the future, 1994, 19 (2), 135–159)

The actually used platelet aggregation inhibitors are acting only on a single agonist. For example, aspirin is active against the arachidonic acid, ticlopidin is active against ADP, hirudin is active against thrombin. The betains of the general formula of the invention disclosed here before are actives against various agonists, as well as on fibrinogen, fibronectin, Von Willebrand factor and other adhesive proteins such as vitronectin, collagen, laminin. This is a major improvement for their efficiency, while preserving the hemostasis mechanism so as to avoid haemorrhagic or bleeding events. Due to their activity by oral administration, said compounds are excellent candidates for pathologies with adhesion of cells between them.

In view of its very low toxicity and its efficiency, the best results have been obtained with glycine betaine (compound of the general formula with n =1). None of the publications to which reference is made in the present specification teach the antagonist activity of the betain with respect to glycoprotein IIb IIIa receptor, nor its activity with respect to adhesive proteins. This antagonist activity is not only limited to the site of glycoprotein IIb IIIa, but also to all the other glycoproteic sites acting in the adhesion of cells of various origins there between.

In the present specification, pharmaceutically acceptable salts are salts of betaine which can be administered, such as salts of betaine with hydrochloric acid, sulfuric acid, sulfonic acid, organic acids such as acetic acid, citric acid, tartaric acid, formic acid, etc., as well as the monohydrate radical.

Betains, preferably glycine betain, is advantageously administered orally, parenterally, sub cutaneously, by suppositories, tablets, capsules, syrup, etc. Administered doses can vary from 0.001 g to 10 g per kg live body, for example from 0.005 g to 5 g, in particular from 0.01 g to 3 g per kg life body.

Examples of administration forms are: tablets, capsules, patches, injectable forms, releasing forms, powder (for example for inhalation therapy, buccal inhalation), syrup, solution (nebulization, for example for inhalation therapy, buccal inhalation). As preferred administration forms, subcutaneous injectable dosage form, patches (to be applied on the skin) and entero soluble oral dosage form, such as gastro insoluble tablets or capsules, etc. provided with an entero soluble coating or matrix or system.

As the pH of an aqueous glycine betaine solution is comprised between about 6 and about 7, an injectable solution (preferably for a subcutaneous injection) can be prepared by mixing solid glycine betaine with water (sterilized and possibly demineralized). The glycine betaine can be in the form of a powder (lyophilized powder) placed in a vial, water is then added to said vial for the preparation of the solution to be injected. If necessary, some acid (such as hydrochloric) can be added to the solution or to the water to be mixed with the powder.

The injectable dosage form can be a pressurized dosage form, such as an air pressurized dosage form. Subcutaneous injectable forms of glycine betaine, such as intravenous injectable forms, are preferred. Glycine betaine injectable forms are for example aqueous solution containing 0.1 to 50% by weight glycine betaine, advantageously from 0.5 to 30%, preferably from 10 to 20%. The injectable form has a pH for example comprised between 5 and 8.5, advantageously from 6 to 7.5, preferably from 6 to 6.5. When the injectable form is prepared by mixing glycine betaine (as a solid form or as a powder form), the pH of the solution is about 6–6.5.

When the glycine betaine is administered by injection, the glycine betaine can be present in a solution of a baxter, for example a baxter for intravenous administration of a saline solution, or a physiological solution, or a blood transfusion baxter.

The invention relate thus also to a baxter for subcutaneous administration (preferably intravenous administration) containing a solution suitable for subcutaneous administration. As more specific example, the baxter contains blood or a blood derivative or a blood portion and glycine betaine for subcutaneous administration.

Another subject matter of the invention is a pharmaceutical composition (such as a tablet) containing insulin and betaine, a pharmaceutical composition (such as a tablet) containing an antibiotic and betaine, a pharmaceutical composition (such as a tablet) containing an anti cancerous agent and betaine, a pharmaceutical composition (such as a tablet) containing aspirin and betaine, etc.

A subject matter of the invention is thus a pharmaceutical combination comprising an effective amount of betaine (preferably glycine betaine) and an effective amount of another active agent for the prevention or treatment of troubles. Advantageously, the pharmaceutical combination comprises an effective amount of an active agent for the treatment and/or prevention of a trouble, said active agent having at least one side effect selected among the group consisting of hemorrhagic events, coagulation troubles, thromboses and associations thereof, and an effective amount of a compound of formula $(CH_3)_3N^+—(CH_2)_n—COO^-$, with n an integer from 1 to 5, preferably equal to 1, for preventing at least 50%, advantageously at least 75%, preferably at least 90%, most preferably substantially completely said troubles and/or for reducing the seriousness of said side effect, advantageously of a factor of at least 50%, preferably of at least 75%, most preferably of at least 90%, especially substantially completely.

Betaine is preferably used as anti hemorrhagic agent in said combination.

The pharmaceutical combination can be in the form of a kit, so as to prepare the combination before administration or during the administration.

Side effect is defined as being events observed more than 2% for the patients in treatment with the active agent. By combining said active agent with betaine, it is possible to reduce drastically said events, for example to less than 2%, as well as the importance or gravity of said events.

The active agent with possible side effect is advantageously selected among the group consisting of contrast agents, anti aggregation agents, anti thrombotic agents, anti cholesterol agents, anti vitamin K and mixtures thereof. Specific examples of such agents are heparine, anti vitamin K, aspirin, agents of the statin family, cerivastatine (Baycol), simvastatin, lovastatin, etc.

The combined pharmaceutical form can be a form in which the active agent and the betaine are administered simultaneously or successively, using the same administration way or different administration ways. As specific examples, when using different administration ways, the betaine is administered in the form of a patch or by subcutaneous injection, while the other active agent is administered by oral way or by injection (subcutaneous,venous). When the combined pharmaceutical form is administered using the same administration way, the dosage form is advantageously an injectable form (such as a venous injectable form), but is preferably a oral dosage form, most preferably a solid or semi-solid dosage form. When using a dosage form, the active agent is advantageously in the form of pellets or micropellets or particles which are coated with a betaine containing layer. The coated particles or pellets can be further be coated with an enterosoluble coating which is gastric insoluble or placed in a matrix or capsule which is enterosoluble and gastric insoluble. Preferably, at least the glycine betaine is in a form suitable for subcutaneous injection (preferably intra venous injection) or in a form adapted for the preparation of a form suitable for subcutaneous injection (preferably intravenous injection).

The invention further relates to a process of treatment of a patient in need or for preventing troubles for a patient, by administering to said patient a therapeutic effective amount of an therapeutic active agent having at least one side effect selected among the group consisting of hemorrhagic events, coagulation troubles, thromboses and associations thereof, in which before and/or during and/or after said administration (preferably before and/or during) said patient is administered a therapeutic effective amount of a compound of formula $(CH_3)_3N^+—(CH_2)_n—COO^-$, with n an integer from 1 to 5, preferably equal to 1, for preventing at least 50%, advantageously at least 75%, preferably at least 90%, most preferably substantially completely said troubles and/or for reducing the seriousness of said side effect, advantageously of a factor of at least 50%, preferably of at least 75%, most preferably of at least 90%, especially substantially completely. Glycine betaine is preferably subcutaneous injected (most preferably intravenous injection)

Apparatus and Method

Material
  Betaine anhydrous, BETAFIN® (Finnsugar Bioproducts, CULTOR, Helinski)
  Rats Wistar, males, weight between 250 and 300 grams
  Sodium Thiopental
  Aggregometer CHRONOLOG COULTRONIC S. A. France
  ADP & collagen Laboratoires Stago France
Methods
  The aggregation is made in accordance to the methods Cardinal & Flower. Pharmacol. Method. 1980. and to American Journal of Clinical Pathology, 1989; 92: 676–679.
Sureney. J D. Whole Blood aggregometry.

After a keeping period of 8 days, the rats are subjected to a fasting for 12 hours. Betain is subcutaneous injected one hour before blood sampling. The rats are then anaesthetized with sodium Thiopental administered at a dose of 200 mg/Kg and the blood samples are taken by intracardiac puncture on a trisodium citrate solution (1 volume of solution at 3,8% citrate for 9 volumes of blood).

Activated Coagulation Time (Kaolin)

This test explores the intrinsic coagulation pathway. One hour after sub cutaneous administration of the betaine, 0.8 ml total blood by intracardiac way is injected in a container HR, HemoTec. These tubes contain the kaolin activator. (Method HemoTec., automated coagulation timer manufactured by MEDTRONIC HEMOTEC Inc., Englewood, Colo., USA).

Induced Hemorrhagic Time IHT

Blood samples are made before the test. The end of the anaesthetized rat tail, is dipped for 5 minutes in a water bath at 37° C. so as to provoke a dilatation of the peripheral vessels which are removed and cut at the end, the chronometer being started. The PHT is defined as being the time period comprised between the cutting of end tail and the end of the hemorrhage or bleeding.

A/Principle of Laser-Induced Thrombosis (Seiffge D. et al., 1989; Weichter W. et al., 1983)

In this model, lesion of the vascular wall is induced by a laser beam. This beam causes a limited lesion of the vascular endothelium (only 1 to 2 cells are destroyed). This laying bare of the sub-endothelium, which is a thrombogenetic surface, results in the adherence of platelets via glycoprotein II. This adherence of platelets is followed by the activation thereof. They form pseudopods and secrete the content of their granules. This activation results in the appearance of glycoproteins IIb-IIIa which are necessary for the aggregation of the platelets between them. This lesion is induced in the mesenteric microcirculation of the rat. It is immediately followed by the formation of a thrombus (in a few seconds). This thrombus, which rapidly enlarges under the influence of the flow of blood, embolises before being formed again.

By this manes, the assessment of the effect of glycine betaine was conducted pharmacologically in conjunction with the study of two active molecules used as a reference; namely acetylsalicylic acid and heparin (of low molecular weight). The assessment also involved the activity of glycine betaine in relation to the prothrombotic effects induced by contrasting products.

B/Stasis-Induced Thrombosis

A laparotomy was performed to open the lower vena cava, on which a ligature was placed at $T_0$, followed by subcutaneous injection of glycine betaine at $T_0+2$ hours, followed by withdrawal of the clot and blood samples at $T_0+6$ hours.

C/Experimental Procedure

Male Wistar rats were used for these tests. They weighed between 200 and 250 grams. After an 8-day stabilisation period, the rats were subjected to fasting for 12 hours. They were than anaesthetised, glycine betaine was administered subcutaneously, and the mesentery (laser) or vena cava (stasis) was opened at the end of the experiments.

EXAMPLES

Example 1

Evaluation of the Number of Emboles and the Duration of Embolisation after Vascular Change Due to Laser Firings

|  | Number of emboles or embolies | Duration of embolisation (minutes) |
|---|---|---|
| Negative control NaCl 0.9% | 5.33 ± 0.58 | 2 ± 0 |
| Glycine betaine 5 mg/kg | 2 ± 0 | 1 ± 0 |
| Acetylsalicylic acid 100 mg/kg | 1 ± 1 | 0.33 ± 0.58 |
| Heparin 2 mg/kg | 2.67 ± 0.52 | 1 ± 0 |

Glycine betaine considerably reduced the number of emboles and the duration of embolisation after vascular change due to laser firings. The results demonstrate its powerful anti-thrombotic activity.

Example 2

Evaluation of the Bleeding Time Caused
(E. Dejana. Bleeding time in rats. Thrombosis. Rech. 1982)

|  | Bleeding time (seconds) |
|---|---|
| Negative control NaCl 0.9% | 101.52 ± 5.7 |
| Glycine betaine 5 mg/kg | 95 ± 5 |
| Acetylsalicylic acid 100 mg/kg | 276.67 ± 20.82 |
| Heparin 2 mg/kg | 313.33 ± 20 |

These results show that glycine betaine maintains the bleeding time which is caused within the values of the negative control. In addition to its anti-thrombotic activity, glycine betaine does not result in any risk of haemorrhage compared with the positive controls.

Example 3

Evaluation of Platelet Aggregation after Vascular Change Due to Laser Firings
(Cardinal & Flower. Pharmacol. Method. 1980)

|  | Amplitude (ohms) | Velocity (ohms/min) |
|---|---|---|
| Negative control NaCl 0.9% | 13 ± 1 | 9 ± 1 |
| Glycine betaine 5 mg/kg | 0.66 ± 1.15 | 1.66 ± 1.15 |
| Acetylsalicylic acid 100 mg/kg | 2.33 ± 2.08 | 2 ± 1 |
| Heparin 2 mg/kg | 4.33 ± 0.57 | 2.66 ± 0.50 |

These results demonstrate the anti-aggregation effect of glycine betaine.

Example 4

Evaluation of the Effect on Blood Cells

| a/Platelet count | |
|---|---|
|  | Number of platelets ($10^9$) |
| Negative control NaCl 0.9% | 788 ± 30.14 |
| Glycine betaine 5 mg/kg | 804.67 ± 20.03 |
| Acetylsalicylic acid 100 mg/kg | 855.33 ± 63.17 |
| Heparin 2 mg/kg | 777.33 ± 6.43 |

-continued b/White corpuscle count

|  | Number of white corpuscles (10⁹) |
|---|---|
| Negative control NaCl 0.9% | 5.03 ± 1 |
| Glycine betaine 5 mg/kg | 4.43 ± 0.32 |
| Acetylsalicylic acid 100 mg/kg | 4.33 ± 1.00 |
| Heparin 2 mg/kg | 5.80 ± 0.10 | c/Red corpuscle count

|  | Number of red corpuscles (10¹²) |
|---|---|
| Negative control NaCl 0.9% | 6.56 ± 0.15 |
| Glycine betaine 5 mg/kg | 6.19 ± 0.25 |
| Acetylsalicylic acid 100 mg/kg | 6.15 ± 0.31 |
| Heparin 2 mg/kg | 6.20 ± 0.20 |

The counts of the elements occurring in the blood remained within the values of the negative control and demonstrated the innocuousness of glycine betaine

Example 5
Biological Balance a/Quick time

|  | QT (seconds) |
|---|---|
| Negative control NaCl 0.9% | 17 ± 1 |
| Glycine betaine 5 mg/kg | 16.9 ± 1.05 |
| Acetylsalicylic acid 100 mg/kg | 18.33 ± 2.08 |
| Heparin 2 mg/kg | 29.50 ± 0.52 | b/Activated cephaline time (ACT)

|  | ACT (seconds) |
|---|---|
| Negative control NaCl 0.9% | 20.5 ± 0.5 |
| Glycine betaine 5 mg/kg | 39.9 ± 1.05 |
| Acetylsalicylic acid 100 mg/kg | 27.26 ± 1.1 |
| Heparin 2 mg/kg | 39.46 ± 1.36 | c/Fibrinogen analysis

|  | Fibrinogen (g/l) |
|---|---|
| Negative control NaCl 0.9% | 2.45 ± 0.19 |
| Glycine betaine 5 mg/kg | 1.7 ± 0.1 |
| Acetylsalicylic acid 100 mg/kg | 2.19 ± 0.33 |
| Heparin 2 mg/kg | 2.13 ± 0.25 | d/Alpha,2-antiplasmin analysis (α2AP)

|  | α2AP (%) |
|---|---|
| Negative control NaCl 0.9% | 30.16 ± 0.85 |
| Glycine betaine 5 mg/kg | 29.7 ± 0.68 |
| Acetylsalicylic acid 100 mg/kg | 29.36 ± 0.92 |
| Heparin 2 mg/kg | 29.4 ± 1.01 | e/Antithrombin III analysis (AT III)

|  | AT III (%) |
|---|---|
| Negative control NaCl 0.9% | 86 ± 3 |
| Glycine betaine 5 mg/kg | 89.5 ± 1.37 |
| Acetylsalicylic acid 100 mg/kg | 85.33 ± 3.51 |
| Heparin 2 mg/kg | 77.66 ± 1.52 |

Example 6
Evaluation of the Activity of Glycine Betaine as a Function of Time Experimental Groups The product was tested at 5 mg/kg Laser-induced thrombosis Control NaCl 0,9%

Group I The product was injected 1 hour before the experiment

Group II The product was injected 2 hours before the experiment

Group III The product was injected 3 hours before the experiment

Group IV The product was injected 4 hours before the experiment a) Effect of the product tested (5 mg/ml/kg) on the bleeding time caused.

| Group | B.T.C. (seconds) |
|---|---|
| NaCl 0.9% | 110 ± 21.2 |
| I | 105 ± 26.2 |
| II | 145 ± 15.52 |
| III | 115.5 ± 14.2 |
| IV | 120 ± 10.13 | b) Effect of the product tested (5 mg/ml/kg) on arterial thrombosis induced by laser beam

| Group | Number of firings | Number of emboles | Duration of embolisation (minutes) |
|---|---|---|---|
| NaCl 0.9% | 2.5 ± 0.84 | 5.7 ± 1.5 | 2.1 ± 0.69 |
| I | 3.49 ± 1.07 | 1.8 ± 1.44 | 0.51 ± 0.5 |
| II | 3.0 ± 1.5 | 1.4 ± 1.18 | 0.3 ± 0.23 |
| III | 2.50 ± 1.25 | 1.99 ± 0.4 | 1.00 ± 0.5 |
| IV | 2.7 ± 1.0 | 2.2 ± 0.69 | 1.5 ± 0.6 | c) Effect of the product tested (5 mg/kg) on platelet aggregation induced ex vivo.

| Group | Amplitude (Ohms) | Velocity (ohm/minute) |
|---|---|---|
| NaCl 0.9% | 24.23 ± 0.5 | 14.4 ± 2.3 |
| I | 11.33 ± 3.08 | 8.2 ± 0.2 |
| II | 13.2 ± 3.5 | 9.3 ± 1.8 |
| III | 12.7 ± 4.1 | 8.7 ± 1.3 |
| IV | 13 ± 2.8 | 8.7 ± 1.15 | d) Evaluation of the effect of glycine betaine on coagulation factors after repeated administration on 5 days of treatment

|  | ACT (seconds) | Quick time (seconds) | Fibrinogen g/l |
|---|---|---|---|
| Untreated control | 21.25 ± 2.3 | 16.1 ± 1.0 | 3.03 ± 0.45 |
| Glycine betaine (5 mg/kg/day) | 39.3 ± 2.3 | 19.8 ± 1.2 | 2.2 ± 0.1 |

Example 7
Evaluation of the Effect of Glycine Betaine on Venous Thrombosis Induced by Stasis a) Effect of glycine betaine on clot weight

|  | Clot weight (mg) |
|---|---|
| Untreated control | 4.033 ± 2 |
| Glycine betaine (1 mg/kg) | 3.1 ± 0.4 |
| Glycine betaine (2.5 mg/kg) | 1.63 ± 0.76 |
| Glycine betaine (5 mg/kg) | 0.76 ± 0.4 | b) Evaluation of the effect of glycine betaine on plasminogenesis

|  | Plasminogenesis % |
|---|---|
| NaCl 0.9% | 2.7 ± 0.33 |
| Glycine betaine (5 mg/kg) | 1.66 ± 0.58 |
| Glycine betaine (2.5 mg/kg) | 2 ± 0.15 |
| Glycine betaine (1 mg/kg) | 2.44 ± 0.58 | c) Evaluation of the effect of glycine betaine on coagulation

|  | ACT (seconds) | Quick time (seconds) | Fibrinogen g/l |
|---|---|---|---|
| Untreated control | 30.2 ± 2.7 | 16.1 ± 1.0 | 3.03 ± 0.45 |
| Glycine betaine (1 mg/kg) | 29.1 ± 2.3 | 16.2 ± 1.2 | 2.63 ± 0.3 |
| Glycine betaine (2.5 mg/kg) | 31.2 ± 2.6 | 16.6 ± 0.7 | 2.2 ± 0.17 |
| Glycine betaine (5 mg/kg) | 33.5 ± 1.9 | 15.6 ± 0.4 | 2.32 ± 0.33 | d) Evaluation of the effect of glycine betaine on coagulation factors

|  | Anti Xa units/ml | Anti IIa units/ml |
|---|---|---|
| Glycine betaine (5 mg/kg) | 0.35 ± 0.15 | — |
| Glycine betaine (2.5 mg/kg) | 0.14 ± 0.10 | — |
| Glycine betaine (1 mg/kg) | 0.08 ± 0.1 | — |

Treatment with glycine betaine inhibits the thromboembolic complications which are initiated by laser firings. In fact, treatment with glycine betaine before laser firings decreases the vascular adherence of platelets and the aggregation thereof.

Treatment with glycine betaine inhibits thrombo-embolic complications. In fact, treatment with glycine betaine before the induction of thrombosis exhibited a high antithrombotic potential with regard to all the parameters which come into play in the process of thrombus formation. Moreover, the results for the biological parameters demonstrate the complete innocuousness of glycine betaine, which, in contrast to the reference products used (aspirin and heparin), does not induce any bleeding effect or undesirable side effect. These features mean that glycine betaine, in addition to its demonstrated efficacy, can be administered to people at risk of haemorrhage as well as to people who would be subject to risk of sensitivity or allergy if given conventional antithrombotic treatments (haemophiliac, allergic). Glycine betaine does not cause thrombopenia or haemorrhagic disorders (Examples 2 & 4). The experimental results of Example 5c shows that there is a consumption of fibrinogen.

It should be noted that, under the same experimental conditions for the preservation of blood, glycine betaine appeared to possess a high anti-coagulant capacity compared with tubes containing heparin or EDTA. The effective dose of glycine betaine appeared to be between 3 and 5 mg per haemolysis tube. This experimental result demonstrates the high anticoagulant potential of glycine betaine. It can thus be claimed that glycine betaine can be used as an anticoagulant both for the treatment of the human body in vivo and for the preservation of blood ex vivo.

Evaluation of the Activity of Glycine Betaine Compared with that of Contrasting Products In the context of our research on the anti-thrombotic effects, and in order to complement our preliminary work on the efficacy of glycine betaine, we evaluated the effect of glycine betaine on the increase of the thrombo-embolic risk associated with the use of contrasting products known for their prothrombotic capacities. The significance of this model is that it enables a direct observation to be made of the formation of a thrombus at the site of the vascular lesion. These results explain the occurrence of thrombotic occlusions during angioplasty, especially amongst patients whose endothelium is already damaged or injured. Coronary angioplasty causes a stripping of the endothelium, exposing collagen, elastin and the smooth muscle cells of the circulating blood, analogously to the experimental thrombosis model employed. Thus, there is a higher incidence of new thrombi amongst patients who have had a recent coronary thrombosis or who have an eccentric coronary plaque.

The administration of contrasting products reduces the number of white corpuscles, the number of red corpuscles and the number of platelets. Contrasting products interact with leukocytes, induce the liberation of leukotrienes, increase vascular permeability and exert a chemotactic effect. Moreover, contrasting products act to control the expression of P-selectin and cause the adherence of white corpuscles to the vascular endothelium. It has been shown that the use of contrasting products is associated with the occurrence of thrombi in variable amounts depending on the product used.

Two contrasting products were studied Hexabrix® (ionic) and ® Iopamidol (non-ionic).

Example 8

Evaluation of Number of Emboles and Duration of Embolisation after Vascular Change Caused by Laser Firings and Administration of Contrasting Products

|  | Number of emboles | Duration of embolisation (minutes) |
|---|---|---|
| Negative control NaCl 0.9% | 5.33 ± 0.58 | 2 ± 0 |
| Hexabrix ® | 8 ± 1 | 3.67 ± 0.58 |
| Iopamidol ® | 11.67 ± 0.50 | 6.33 ± 0.52 |
| Glycine betaine 5 mg/kg + Hexabrix ® | 4 ± 1 | 2 ± 0 |
| Glycine betaine 5 mg/kg + Iopamidol ® | 5.33 ± 0.58 | 2.33 ± 0.48 |

Example 9
Evaluation of Induced Bleeding Time (IBD)

|  | IBD (seconds) |
|---|---|
| Negative control NaCl 0.9% | 101.52 ± 5.7 |
| Hexabrix ® | 195 ± 13.23 |
| Iopamidol ® | 128 ± 7.64 |
| Glycine betaine 5 mg/kg + Hexabrix ® | 150 ± 5 |
| Glycine betaine 5 mg/kg + Iopamidol ® | 111 ± 6.60 |

This example shows a reduction of the induced bleeding time of contrasting agents, and an antihemorrhagic effect of the betaine.

Example 10
Evaluation of Platelet Aggregation after Vascular Change Due to Laser Firings

|  | Amplitude (ohm) | Velocity (ohm/min) |
|---|---|---|
| Negative control NaCl 0.9% | 13 ± 1 | 9 ± 1 |
| Hexabrix ® | 6 ± 1 | 5.66 ± 0.57 |
| Iopamidol ®~ | 15 ± 2.64 | 12.33 ± 0.50 |
| Glycine betaine 5 mg/kg + Hexabrix ® | 2 ± 1 | 5 ± 0 |
| Glycine betaine 5 mg/kg + Iopamidol ® | 4.66 ± 0.52 | 9.33 ± 0.8 |

Example 11
Evaluation of the Effect of Glycine Betaine on Blood Cells

| a/ Platelet count | Number of platelets ($10^9$) |
|---|---|
| Negative control NaCl 0.9% | 788.33 ± 30.14 |
| Hexabrix ® | 620 ± 10 |
| Iopamidol ® | 585.67 ± 23.54 |
| Glycine betaine 5 mg/kg + Hexabrix ® | 669.67 ± 7.37 |
| Glycine betaine 5 mg/kg + Iopamidol ® | 704.33 ± 92.33 |

| b/ White corpuscle count | Number of white corpuscles ($10^{12}$) |
|---|---|
| Negative control NaCl 0.9% | 5.03 ± 0.20 |
| Hexabrix ® | 2.96 ± 0.21 |
| Iopamidol ® | 3.06 ± 0.35 |
| Glycine betaine 5 mg/kg + Hexabrix ® | 4.20 ± 0.1 |
| Glycine betaine 5 mg/kg + Iopamidol ® | 3.9 ± 0.3 |

| c/ Red corpuscle count | Number of red corpuscles ($10^9$) |
|---|---|
| Negative control NaCl 0.9% | 6.56 ± 0.15 |
| Hexabrix ® | 5.43 ± 0.47 |
| Iopamidol ® | 5.5 ± 0.36 |
| Glycine betaine 5 mg/kg + Hexabrix ® | 6.5 ± 0.15 |
| Glycine betaine 5 mg/kg + Iopamidol ® | 6.6 ± 0.19 |

Example 12
Biological Balance

| a/ Quick time | QT (seconds) |
|---|---|
| Negative control NaCl 0.9% | 17 ± 1 |
| Hexabrix ® | 24.13 ± 1 |
| Iopamidol ® | 28.1 ± 0.75 |
| Glycine betaine 5 mg/kg + Hexabrix ® | 16.36 ± 0.56 |
| Glycine betaine 5 mg/kg + Iopamidol ® | 17.83 ± 1.2 |

| b/ Activated cephaline time (ACT) | ACT (seconds) |
|---|---|
| Negative control NaCl 0.9% | 20.5 ± 0.5 |
| Hexabrix ® | 49.3 ± 1.85 |
| Iopamidol ® | 41.33 ± 0.8 |
| Glycine betaine 5 mg/kg + Hexabrix ® | 25.4 ± 0.61 |
| Glycine betaine 5 mg/kg Iopamidol ® | 22.4 ± 0.7 |

| c/ Fibrinogen analysis | Fibrinogen (g/l) |
|---|---|
| Negative control NaCl 0.9% | 2.45 ± 0.19 |
| Hexabrix ® | 1.49 ± 0.18 |
| Iopamidol ® | 1.5 ± 0.8 |
| Glycine betaine 5 mg/kg + Hexabrix ® | 1.7 ± 0.09 |
| Glycine betaine 5 mg/kg Iopamidol ® | 1.9 ± 0.1 |

| d/ Alpha,2-antiplasmin analysis (α2AP) | α2AP (%) |
|---|---|
| Negative control NaCl 0.9% | 30.16 ± 0.85 |
| Hexabrix ® | 23.26 ± 1.06 |
| Iopamidol ® | 25.23 ± 0.95 |
| Glycine betaine 5 mg/kg + Hexabrix ® | 25.66 ± 0.09 |
| Glycine betaine 5 mg/kg Iopamidol ® | 28.13 ± 0.8 |

| e/ Antithrombin III analysis (AT III) | AT III (%) |
|---|---|
| Negative control NaCl 0.9% | 86.3 ± 3 |
| Hexabrix ® | 81.63 ± 0.66 |
| Iopamidol ® | 70.6 ± 1.51 |
| Glycine betaine 5 mg/kg + Hexabrix ® | 79.1 ± 1.05 |
| Glycine betaine 5 mg/kg Iopamidol ® | 87.26 ± 0.98 |

Treatment with glycine betaine inhibits the thromboembolic complications associated with the use of contrasting products. In fact, treatment with glycine betaine, before or during the injection of contrasting products, reduces the adherence of platelets and their aggregation at vascular level. These results demonstrate the anti-thrombotic and thrombolytic effects of glycine betaine. It should be noted that the contrasting products can have other side effects such as haemostasis in catheters and endothelial lesions due to the administration procedures themselves. Glycine betaine remedies these undesirable effects.

Conclusion

Glycine betaine possesses the same, or even better, therapeutic features as those of the anticoagulants and antiaggregants investigated (acetylsalicylic acid and heparin), whilst exhibiting no undesirable effects.

The superior performance as regards therapeutic efficacy of glycine betaine in relation to these two molecules (acetylsalicylic acid and heparin) is an incentive for the formulation of a drug containing glycine betaine as a therapeutically active ingredient, said drug being intended for the treatment of thromboses and thrombo-embolic diseases.

According the results presented above, this drug also exhibits anticoagulant, anti-aggregant and fibrinolytic indications. The demonstrated innocuousness of this molecule enables long-term treatments to be considered which do not necessitate biological monitoring.

Interest in the use of glycine betaine is based on the fact that it acts at several levels of haemostatis, i.e. it acts on platelet aggregation, coagulation and fibrinolysis. This activity is durable and prevents repeated administration, which constitutes a considerable improvement in relation to existing treatments. The administration of betaine does not induce any haemorrhagic risk or other side effects (e.g. heparin-induced thrombopenia), which constitutes a major advance in antithrombotic therapy.

Example 13

Aggregation Induced with ADP

Final ADP concentration 5 $\mu$M

|  | Amplitude (ohms) | Velocity (ohm/minute) |
| --- | --- | --- |
| Control NaCl 0.9% | 16.4 +/− 1.67 | 13.8 +/− 1.3 |
| Glycine betaine 2.5 mg/kg | 13 +/− 0.82 | 5.75 +/− 0.96 |
| Glycine betaine 5 mg/kg | 7.25 +/− 0.96 | 4.75 +/− 0.5 |
| Glycine betaine 10 mg/kg | 0 +/− 0 | 0 +/− 0 |

The dose effect of the betaine shows its action on the glycoprotein IIb IIIa site, the betaine competing in a dose dependant manner with the agonist (ADP).

Example 14

Aggregation Induced with Collagen

Collagen concentration 10 $\mu$gr/ml

|  | Amplitude (ohms) | Velocity (ohm/minute) |
| --- | --- | --- |
| Control NaCl 0.9% | 16.75 +/− 0.96 | 9.75 +/− 0.98 |
| Glycine betaine 2.5 mg/kg | 13.75 +/− 0.96 | 9.25 +/− 2.63 |
| Glycine betaine 5 mg/kg | 5.5 +/− 1.29 | 4.5 +/− 1 |
| Glycine betaine 10 mg/kg | 1.5 +/− 1.29 | 2 +/− 0.82 |

The dose effect of the betaine shows its action on the glycoprotein IIb IIIa site, the betain competing in a dose dependant manner with the agonist (Collagen).

Example 14

Activated Coagulation Time (Subcutaneous Administration of Betain at Different Dosages)

|  | Activated Coagulation time (seconds) | Provoked Hemorrhagy time (seconds) |
| --- | --- | --- |
| Control NaCl 0.9% | 48 | 107 |
| Glycine betaine 10 mg/kg | 128 | 105 |
| Glycine betaine 30 mg/kg | 179 | 112 |
| Glycine betaine 50 mg/kg | 215 | 115 |

The activated coagulation time is four time higher at a concentration of 50 mg/kg, while not having an effect on the PHT.

Example 15

Activated Coagulation Time after Subcutaneous Administration of Betaine at 10 mg/kg after 24 Hours

|  | Provoked hemorrhage seconds | Activated coagulation time (seconds) |
| --- | --- | --- |
| Control NaCl 0.9% | 105 +/− 5 | 48.4 +/− 8.9 |
| Betaine 10 mg/kg | 114 +/− 12.76 | 71 +/− 3.51 |

Example 16

Parameters of Thrombosis Induced by Laser 24 Hours after Sub Cutaneous Administration of Betaine at 10 mg/kg

|  | Number of laser firing | Number of emboles | Embolisation time (minutes) |
| --- | --- | --- | --- |
| Control NaCl 0.9% | 2.33 +/− 0.57 | 5.33 +/− 0.57 | 2 +/− 0 |
| Betain 10 mg/kg | 3.33 +/− 0.57 | 1 +/− 0 | 0 +/− 0 |

Example 17

Activated Coagulation Time after Subcutaneous Administration of Betaine at 20 mg/kg after 24 Hours

|  | Provoked hemorrhage seconds | Activated coagulation time (seconds) |
| --- | --- | --- |
| Control NaCl 0.9% | 105 +/− 5 | 48.4 +/− 8.9 |
| Betaine 20 mg/kg | 110 +/− 13.22 | 154.66 +/− 11.01 |

Example 18
Parameters of Thrombosis Induced by Laser 24 Hours after Sub Cutaneous Administration of Betaine at 20 mg/kg

|  | Number of laser firing | Number of emboles | Embolisation time (minutes) |
|---|---|---|---|
| Control NaCl 0.9% | 2.33 +/- 0.57 | 5.33 +/- 0.57 | 2 +/- 0 |
| Betain 10 mg/kg | 3.33 +/- 0.57 | 0.66 +/- 0.57 | 0 +/- 0 |

Example 19
Kinetic of the Activated Coagulation Time after Oral Administration of Betain at 50 mg/kg

|  | Induced hemorrhage seconds | Activated coagulation time (seconds) |
|---|---|---|
| Control NaCl 0.9% | 105 +/- 5 | 48.4 +/- 8.9 |
| Betaine 50 mg/kg - 1 hour | 120 +/- 5 | 96 +/- 11.27 |
| Betaine 50 mg/kg - 6 hours | 111 +/- 3.6 | 124.66 +/- 9.29 |
| Betaine 50 mg/kg - 24 hours | 113.33 +/- 18.92 | 64.66 +/- 7.37 |
| Betaine 50 mg/kg - 48 hours | 109 +/- 8.54 | 55.66 +/- 7.02 |

Example 20
Kinetic of Parameters of Thrombosis Induced by Laser and Effect at Different Time for the Oral Administration of Betaine at 50 mg/kg

|  | Number of laser firing | Number of emboles | Embolisation time (minutes) |
|---|---|---|---|
| Control NaCl 0.9% | 2.33 +/- 0.57 | 5.33 +/- 0.57 | 2 +/- 0 |
| Betain 50 mg/kg 1 hour | 4 +/- 0 | 0 +/- 0 | 0 +/- 0 |
| Betain 50 mg/kg 6 hours | 3.66 +/- 0.57 | 2.33 +/- 0.57 | 1 +/- 0 |
| Betain 50 mg/kg 24 hours | 2.33 +/- 0.57 | 2.33 +/- 0.57 | 1 +/- 0 |
| Betain 50 mg/kg 48 hours | 2.33 +/- 0.57 | 4.33 +/- 0.57 | 2 +/- 0 |

The dose effect is confirmed in all the studied parameters. The antagonist activity at the glycoprotein IIb IIIa site for the compounds of the invention also applies to other agonists, such as serotinin, arachidonic acid, epinephrine, adrenaline, ristocetine and thrombin.

Example 21
Human In Vivo Test

Two volunteers (with a weight of about 70–75 kg), considered as heavy smokers (smoking more than 10 cigarettes/day) have orally taken capsules (gastro soluble) containing 5 g anhydrous glycine betaine/day during 7 days.

Before administration of the betaine, the aggregations induced by ADP, by collagen, by epinephrine, by adrenaline, by thrombin, by ristocetine and by arachidonic acid were determined. After one week treatment, the same platelet aggregations were measured. It appears from said tests that all the induced platelet aggregations were reduced for all said endogenous agonists of at least 30%.

Better results are expected when using oral dosage form with controlled release, such as gastro insoluble, but entero soluble form.

Example 22
Antihemorrhagic Activity

Rats have been used in this test. Some rats received an active agent with hemorrhagic side effect, while other rats received said active agent together with a dose of betaine.

The following products were administered to rats for determining whether glycine betaine has an antihemorrhagic effect:

100 mg aspirine per kg life body
100 mg aspirine+50 mg glycine betaine per kg life body
2 mg heparine
2 mg heparine+50 mg glycine betaine When inducing a hemorrhage, it was observed that the bleeding time was reduced when glycine betaine was administered. It means therefore that glycine betaine has antihemorrhagic properties.

In view of the above specification, the invention relates thus also to:

the use of a compound of formula $(CH_3)_3N^+$—$(CH_2)_n$—$COO^-$ with n an integer from 1 to 5, preferably equal to 1, or a mixture of such compounds or one or more pharmaceutically acceptable salts thereof for the preparation of a pharmaceutical composition for the treatment or the prevention of troubles bound to one or more glycoproteins, especially to receptor of one or more glycoproteins, preferably to receptor of glycoprotein IIb IIIa, the use of a compound of formula $(CH_3)_3N^-$—$(CH_2)_n$—$COO^-$ with n an integer from 1 to 5, preferably equal to 1, or a mixture of such compounds or one or more pharmaceutically acceptable salts thereof for the preparation of a pharmaceutical composition for the treatment or the prevention of troubles bound to one or more glycoproteins, especially to receptor of one or more glycoproteins, preferably to receptor of glycoprotein IIb IIIa for inhibiting the platelet aggregation, the use of a compound of formula $(CH_3)_3N^+$—$(CH_2)_n$—$COO^-$ with n an integer from 1 to 5, preferably equal to 1, or a mixture of such compounds or one or more pharmaceutically acceptable salts thereof for the preparation of a pharmaceutical composition for the treatment or the prevention of troubles bound to one or more glycoproteins, especially to receptor of one or more glycoproteins, preferably to receptor of glycoprotein IIb IIIa for avoiding the adhesion of cells there between Pharmaceutical composition comprising insulin and at least a compound of formula $(CH_3)_3N^+(CH_2)_nCOO^-$ with n an integer from 1 to 5, preferably equal to 1, or a mixture of such compounds or one or more pharmaceutically acceptable salts thereof Pharmaceutical composition comprising an anticancerous agent and at least a compound of formula $(CH_3)_3N^+(CH_2)_nCOO^-$ with n an integer from 1 to 5, preferably equal to 1, or a mixture of such compounds or one or more pharmaceutically acceptable salts thereof Pharmaceutical composition comprising an antibiotic and at least a compound of formula $(CH_3)_3N^+(CH_2)_nCOO^-$ with n an integer from 1 to 5, preferably equal to 1, or a mixture of such compounds or one or more pharmaceutically acceptable salts thereof Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as glycoproteic antagonist agent, in particular as antagonist of the glycoprotein IIb IIIa, for the preparation of a pharmaceutical composition Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to cancer, in particular to the metastasis of cancerous cells Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to blood circulation, in particular to the blood microcirculation Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to nicotine addiction Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to obesity Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutically active agent for the preparation of a pharmaceutical composition for the treatment or the prevention or the stabilization of troubles bound to hemophilia Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to chemotherapy Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of diabetic troubles Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to aging Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to oestrogen oral contraception Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutically active agent for the preparation of a pharmaceutical composition for the treatment or the prevention or the stabilization of troubles bound to extracorporal blood circulation, in particular to troubles bound to dialysis and to hemodialysis Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to inflammation, in particular internal inflammation troubles Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to bites, in particular to bites of venomous animals, Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to post traumatic shock or post surgical shock, Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to septic shocks, Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to hemorrhage, in particular to internal hemorrhage, such as a cerebral hemorrhage, Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to embolism, in particular to cerebral embolism and/or pulmonary embolism Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to an infract Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutically active agent for the preparation of a pharmaceutical composition for the treatment or the prevention or the stabilization of troubles bound to aneurysm Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to phlebitis Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to angina pectoris Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of thromboses troubles, in particular troubles bound to reocclusion of the vascular system and/or to thrombolysis and/or to angioplasty Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to the use of hemoplastic or hemostatic glues, in particular fibrinogen glue, fibrin glue, collagen glue, thrombin glue Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to pregnancy Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of thromboses troubles, in particular coronary thrombosis and/or venous thrombosis Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to trip or travel, in particular travel in airplane, buses, trains, racket, space shuttle, preferably travel at speed of more than 200 km/h Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to travel, in particular to travel in pressurized environment Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of bacterial troubles and/or infectious troubles and/or troubles due to virus and/or troubles due to fongus Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of asthmatic troubles Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to osteoporosis Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as therapeutic active agent for the preparation of a pharmaceutical composition for the treatment or the prevention or the stabilization of troubles bound to graft of skin and/or tissue and/or bone and/or cells Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as antagonist agent for serotinin and/or arachidonic acid and/or epinephrine and/or adrenaline and/or thrombin and/or ristocetine for the preparation of a pharmaceutical composition Uses as disclosed here before for the preparation of a pharmaceutical form, possibly as a kit, containing an active agent different from compound of formula $(CH_3)_3N^+(CH_2)_nCOO^-$ with n an integer from 1 to 5, preferably equal to 1, or a mixture of such compounds or one or more pharmaceutically acceptable salts thereof, for the administration (simultaneous or successive, with the same or different administration path) of said other therapeutic active agent and of a compound of formula $(CH_3)_3N^+(CH_2)_nCOO^-$ with n an integer from 1 to 5, preferably equal to 1, or a mixture of such compounds or one or more pharmaceutically acceptable salts thereof Sweetening composition containing at least a sweetener and at least a compound of formula $(CH_3)_3N^+(CH_2)_nCOO^-$ with n an integer from 1 to 5, preferably equal to 1, or a mixture of such compounds or one or more pharmaceutically acceptable salts thereof Sweetening composition containing at least a compound of formula $(CH_3)_3N^+(CH_2)_nCOO^-$ with n an integer from 1 to 5, preferably equal to 1, or a mixture of such compounds or one or more pharmaceutically acceptable salts thereof Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as agent for improving the sweetening property of a sweetener, in particular of a synthetic sweetener Process for detecting and/or localizing and/or separating thrombi in vitro and/or in vivo, possibly in an extra corporal loop or circuit, in which blood is mixed or added with at least a compound of formula $(CH_3)_3N^+(CH_2)_nCOO^-$ with n an integer from 1 to 5, preferably equal to 1, or a mixture of such compounds or one or more pharmaceutically acceptable salts thereof Preserving process for cells and/or platelets in a medium, in particular in a blood medium or a fraction thereof, in which said medium is added or mixed with compound of formula $(CH_3)_3N^+(CH_2)_nCOO^-$ with n an integer from 1 to 5, preferably equal to 1, or a mixture of such compounds or one or more pharmaceutically acceptable salts thereof Process for the isolation and/or individualisation of cells and/or platelets in a medium, in particular in a blood medium or a fraction thereof, in which said medium is added or mixed with at least a compound of formula $(CH_3)_3N^+(CH_2)_nCOO^-$ with n an integer from 1 to 5, preferably equal to 1, or a mixture of such compounds or one or more pharmaceutically acceptable salts thereof Platelet rich plasma (blood plasma) or platelet poor plasma, said plasma containing at least a compound of formula $(CH_3)_3N^+(CH_2)_nCOO^-$ with n an integer from 1 to 5, preferably equal to 1, or a mixture of such compounds or one or more pharmaceutically acceptable salts thereof Process for the culture of cells in a medium or on a support or in a bioreactor, in particular in a blood medium or a fraction thereof, in which said medium is added or mixed with at least a compound of formula $(CH_3)_3N^+(CH_2)_nCOO^-$ with n an integer from 1 to 5, preferably equal to 1, or a mixture of such compounds or one or more pharmaceutically acceptable salts thereof Process for the preparation of fibrin and/or collagen by reaction of fibrinogen or collagen in presence of at least a compound of formula $(CH_3)_3N^+(CH_2)_nCOO^-$ with n an integer from 1 to 5, preferably equal to 1, or a mixture of such compounds or one or more pharmaceutically acceptable salts thereof glue (such as a hemostatic glue) containing at least a compound of formula $(CH_3)_3N^+(CH_2)_nCOO^-$ with n an integer from 1 to 5, preferably equal to 1, or a mixture of such compounds or one or more pharmaceutically acceptable salts thereof Device with a surface in contact with fibrin and/or fibrinogen and/or collagen, said surface being made of and being treated with a composition containing at least a compound of formula $(CH_3)_3N^+(CH_2)_nCOO^-$ with n an integer from 1 to 5, preferably equal to 1, or a mixture of such compounds or one or more pharmaceutically acceptable salts thereof Composition containing at least fibrinogen and at least a compound of formula $(CH_3)_3N^+(CH_2)_nCOO^-$ with n an integer from 1 to 5, preferably equal to 1, or a mixture of such compounds or one or more pharmaceutically acceptable salts thereof Composition containing at least collagen and at least a compound of formula $(CH_3)_3N^+(CH_2)_nCOO^-$ with n an integer from 1 to 5, preferably equal to 1, or a mixture of such compounds or one or more pharmaceutically acceptable salts thereof Process for the treatment of blood or a fraction thereof by osmosis and/or reverse osmosis, in which, before and/or during and/or after the osmosis or reverse osmosis, said blood is added or mixed with at least a compound of formula $(CH_3)_3N^+(CH_2)_nCOO^-$ with n an integer from 1 to 5, preferably equal to 1, or a mixture of such compounds or one or more pharmaceutically acceptable salts thereof Process for the treatment of blood or a fraction thereof by centrifugation, in which, before and/or during and/or after the centrifugation, said blood is added or mixed with at least a compound of formula $(CH_3)_3N^+(CH_2)_nCOO^-$ with n an integer from 1 to 5, preferably equal to 1, or a mixture of such compounds or one or more pharmaceutically acceptable salts thereof Use of a compound of formula $(CH_3)_3N^+(CH_2)_nCOO^-$ with n an integer from 1 to 5, preferably equal to 1, or a mixture of such compounds or one or more pharmaceutically acceptable salts thereof for the preparation of a pharmaceutical or cosmetic composition for the treatment or prevention or stabilization of hair troubles, in particular troubles due to hair losses Biological material or synthetic material for implant purposes, especially for bone implant, said material being treated with a compound of formula $(CH_3)_3N^+(CH_2)_nCOO^-$ with n an integer from 1 to 5, preferably equal to 1, or a mixture of such compounds or one or more pharmaceutically acceptable salts thereof, and/or a composition containing such a compound Process of treatment of a patient suffering of a trouble cited hereabove in this specification, in which an effective amount of a compound of formula $(CH_3)_3N^+(CH_2)_nCOO^-$ with n an integer from 1 to 5, preferably equal to 1, or a mixture of such compounds or one or more pharmaceutically acceptable salts thereof is administered to said patient, so as to treat and/or stabilize said trouble Process for preventing a patient to suffer a trouble cited hereabove in this specification, in which an effective amount of a compound of formula $(CH_3)_3N^+(CH_2)_nCOO^-$ with n an integer from 1 to 5, preferably equal to 1, or a mixture of such compounds or one or more pharmaceutically acceptable salts thereof is administered to said patient, so as to prevent said trouble, Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as antiagglutinant agent, for the preparation of a pharmaceutical composition Use of a compound of formula $(CH_3)_3N^+(CH_2)_nCOO^-$ with n an integer from 1 to 5, preferably equal to 1, or a mixture of such compounds or one or more pharmaceutically acceptable salts thereof, as blood fluidifying agent, for the preparation of a pharmaceutical composition.

What is claimed is:

1. Method for treating a human at risk to suffer from thrombosis of arterial or venous origin not induced by hyperhomocysteinuria or homocystinuria, said method comprising the step of administering daily a therapeutically effective amount of glycine betaine as an anti thrombotic agent, said administering step being carried out by a form selected from the group of an oral dosage form, a subcutaneous injectable dosage form and patches.

2. The method of claim 1, in which the glycine betaine is administered with a pharmaceutically acceptable support, vehicle or excipient.

3. The method of claim 1, in which the glycine betaine is administered by subcutaneous injection.

4. Method for treating a human at risk to suffer from thrombo-embolic diseases of arterial or venous origin not induced by hyperhomocysteinuria or homocystinuria, said method comprising the step of administering daily a therapeutically effective amount of glycine betaine as antithrombotic agent, said administering step being carried out by a form selected from the group consisting of an oral dosage form, a subcutaneous injectable dosage form and patches.

5. The method of claim 4, in which the glycine betaine is administered with a pharmaceutically acceptable support, vehicle or excipient.

6. The method of claim 4, in which the glycine betaine is administered by subcutaneous injection.

7. Method for treating a human at risk to suffer from blood coagulation disorders, said method comprising the step of administering daily a therapeutically effective amount of glycine betaine as an antithrombotic agent, said administering step being carried out by a form selected from the group consisting of an oral dosage form, a subcutaneous injectable dosage form and patches.

8. The method of claim 7, in which the glycine betaine is administered with a pharmaceutically acceptable support, vehicle or excipient.

9. The method of claim 7, in which the glycine betaine is administered with a pharmaceutically acceptable support, vehicle or excipient.

10. The method of claim 7, for the treatment of platelet aggregation disorders.

11. The method of claim 7, for the treatment of hemorrhage disorders.

12. Method of treating a human at risk to suffer from throboses and with hemorrhage risk, said method comprising the step of administering daily a therapeutically effective amount of glycine betaine as antithrombotic agent, said administering step being carried out by a form selected from the group consisting of an oral dosage form, a subcutaneous injectable dosage form and patches.

13. The method of claim 12, in which the glycine betaine is administered with a pharmaceutically acceptable support, vehicle or excipient.

14. The method of claim 12, in which the glycine betaine is administered by subcutaneous injection.

15. Method of lysing thrombus in a patient, said method comprising the step of administering a therapeutically effective amount of glycine betaine as lysing agent, said administering step being carried out by a form selected from the group consisting of an oral dosage form, a subcutaneous injectable dosage form and patches.

16. The method of claim 15, in which the glycine betaine is administered with a pharmaceutically acceptable support, vehicle or excipient.

17. The method of claim 15, in which the glycine betaine is administered by subcutaneous injection.

18. Method of counteracting thrombo-embolic effects induced by a contrasting product administered to a human, said method comprising the step of administering a therapeutically effective amount of glycine betaine as counteracting agent against thrombo-embolic effects induced by the administered contrasting agent, said administering step being carried out by a form selected from the group consisting of an oral dosage form, a subcutaneous injectable dosage form, and patches.

19. The method of claim 18, in which the glycine betaine is administered with a pharmaceutically acceptable support, vehicle or excipient.

20. The method of claim 18, in which the glycine betaine is administered by subcutaneous injection.

21. A method for lessening the incidence of hemorrhagic side effects in a human associated with the administration of an antithrombotic active agent other than glycine betaine, wherein the method comprises the step of administering an effective amount of glycine betaine as lessening agent of the incidence of hemorrhagic side effects due to the administration of said antithrombotic active agent, said administering step being carried out by a form selected from the group consisting of an oral dosage form, a subcutaneous injectable dosage form and patches.

22. The method of claim 21, in which the glycine betaine is administered with a pharmaceutically acceptable support, vehicle or excipient.

23. The method of claim 21, in which the glycine betaine is administered by subcutaneous injection.

24. Method of treating thromboses not induced by hyperhomocysteinuria or homocystinuria in a human, said method comprising the step of administering daily a therapeutically effective amount of glycine betaine as an antithrombotic agent, said administering step being carried out by a form selected from the group consisting of an oral dosage form, a subcutaneous injectable dosage form and patches.

25. Method of treating a human suffering from blood coagulation disorders, said method comprising the step of administering a therapeutically effective amount of glycine betaine for reducing the activation of constituents of blood and for reducing the activation of coagulation resulting in the formation of thrombin, said administering step being carried out by a form selected from the group consisting of an oral dosage form, a subcutaneous injectable dosage form and patches.

26. The method of claim 1, in which the glycine betaine is administered in the form of a controlled oral dosage form.

27. The method of claim 4, in which the glycine betaine is administered in the form of a controlled oral dosage form.

28. The method of claim 7, in which the glycine betaine is administered in the form of a controlled oral dosage form.

29. The method of claim 12, in which the glycine betaine is administered in the form of a controlled oral dosage form.

30. The method of claim 15, in which the glycine betaine is administered in the form of a controlled oral dosage form.

31. The method of claim 18, in which the glycine betaine is administered in the form of a controlled oral dosage form.

32. The method of claim 21, in which the glycine betaine is administered in the form of a controlled oral dosage form.

33. The method of claim 24, in which the glycine betaine is administered in the form of a controlled oral dosage form.

34. The method of claim 25, in which the glycine betaine is administered in the form of a controlled oral dosage form.

35. Method of treating a human at risk to suffer from blood coagulation disorders as defined by Virshow, said method comprising the step of administering daily a therapeutically effective amount of glycine betaine as an antithrombotic agent, said administering step being carried out by a form selected from the group consisting of an oral dosage form, subcutaneous injectable dosage form and patches.

36. The method of claim 35, in which the glycine betaine is administered with a pharmaceutically acceptable support, vehicle or excipient.

37. The method of claim 35, in which the glycine betaine is administered by subcutaneous injection.

38. The method of claim 35, for the treatment of platelet aggregation disorders.

39. The method of claim 35, in which the glycine betaine is administered in the form of a controlled oral dosage form.

40. Method of treating a human suffering from thrombin formation, said method comprising the step of administering daily a therapeutically effective amount of glycine betaine as antithrombotic agent for reducing the activation of blood coagulation or thrombin formation, said administering step being carried out by a form selected from the group consisting or an oral dosage form, a subcutaneous injectable dosage form and patches.

41. Method of treating a human suffering of a blood hypercoagulable state as defined by Virchow, said method comprising the step of administering daily a therapeutically effective amount of glycine betaine to said human, said administering step being carried out by a form selected from the group consisting of an oral dosage form, a subcutaneous injectable dosage form and patches.

42. Method of treating a human at risk to suffer of a blood hypercoagulable state as defined by Virchow, said method comprising the step of administering daily a therapeutically effective amount of glycine betaine to said human, said administering step being carried out by a form selected from the group consisting of an oral dosage form, a subcutaneous injectable dosage form and patches.

43. Method of treating a human at risk to suffer from blood coagulation activation, said method comprising the step of administering daily a therapeutically effective amount of glycine betaine as antithrombotic agent, said administering step being carried out by a form selected from the group consisting of an oral dosage form a subcutaneous injectable dosage form and patches.

44. The method of claim 7, in which the glycine betaine is administered for reducing the activation of constituents of blood and/or for reducing the activation of coagulation resulting in the formation of thrombin.

45. Method of threating humans suffering from a disease selected from the group consisting of thrombosis, thrombo-embolic diseases, blood coagulation activation disorders, said humans with risk of undergoing hemorrhage, wherein the method comprises the step of administering daily a therapeutically effective amount of glycine betaine as antithrombotic agent, said administering step being carried out by a form selected from the group consisting of an oral dosage form, a subcutaneous injectable dosage form and patches.

46. Method of treating humans suffering from thrombin formation, said humans with risk of undergoing hemorrhage, wherein the method comprises the step of administering daily a therapeutically effective amount of glycine betaine as antithrombotic agent, said administering step being carried out by a form selected from the group consisting of an oral dosage form, a subcutaneous injectable dosage form and patches.

47. Method of threating humans at risk to suffer from a disease selected from the group consisting of thrombosis, thrombo-embolic diseases, blood coagulation activation disorders, said patients with risk of undergoing hemorrhage, wherein the method comprises the step of administering daily a therapeutically effective amount of glycine betaine as antithrombotic agent, said administering step being carried out by a form selected from the group consisting of an oral dosage form, a subcutaneous injectable dosage form and patches.

48. Method of lysing thrombus in a human, said method comprising the step of administering a therapeutically effective amount of glycine betaine as a fibrinolytic agent, said administering step being carried out by a form selected from the group consisting of an oral dosage form, a subcutaneous injectable dosage form and patches.

* * * * *